United States Patent
Riedel

[19]

[11] Patent Number: 6,150,124
[45] Date of Patent: Nov. 21, 2000

[54] METHOD FOR PASSIVELY DETERMINING THE APPLICATION OF A SAMPLE FLUID ON AN ANALYTE STRIP

[75] Inventor: Richard Riedel, Carmel, Ind.

[73] Assignee: UMM Electronics, Inc., Indianapolis, Ind.

[21] Appl. No.: 09/315,700

[22] Filed: May 20, 1999

[51] Int. Cl.[7] .............................. C12Q 1/54; C12Q 1/00
[52] U.S. Cl. ................................ 435/14; 435/970; 435/4
[58] Field of Search ................... 435/14, 970, 4

[56] References Cited

U.S. PATENT DOCUMENTS

| | | | |
|---|---|---|---|
| 5,049,487 | 9/1991 | Phillips et al. | 435/14 |
| 5,179,005 | 1/1993 | Phillips et al. | 435/14 |
| 5,344,754 | 9/1994 | Zweig | 435/14 |
| 5,352,351 | 10/1994 | White et al. | 435/14 |
| 5,426,032 | 6/1995 | Phillips et al. | 435/14 |
| 5,431,880 | 7/1995 | Kramer | 435/14 |
| 5,801,817 | 9/1998 | Riedel | 435/14 |

FOREIGN PATENT DOCUMENTS

| | | |
|---|---|---|
| 0922954A2 | 6/1999 | European Pat. Off. . |
| 19629992 | 1/1998 | Germany . |

*Primary Examiner*—Louise N. Leary
*Attorney, Agent, or Firm*—Woodard, Emhardt, Naughton Moriarty & McNett

[57] ABSTRACT

The present invention relates to a method for passively determining the application of a sample fluid on an analyte strip using measurement of ambient light passing through the strip. Sample fluid, such as whole blood, is applied to a reagent matrix and the amount of ambient light transmitted through the matrix is periodically measured both before and after application of the sample fluid. A step increase of the transmitted light reading occurs after hydration of the strip, and the occurrence of this step increase is used to start a predetermined incubation period. At the expiration of the incubation period, another light transmission measurement is made which is indicative of an analyte concentration in the sample fluid (such as glucose concentration in a whole blood sample).

7 Claims, 6 Drawing Sheets

METHOD FOR PASSIVELY DETERMINING THE APPLICATION OF A SAMPLE FLUID ON AN ANALYTE STRIP

TECHNICAL FIELD OF THE INVENTION

The present invention generally relates to a method for determining the application of chemical and biochemical components (analytes) in aqueous fluids on an analyte test strip and, more particularly, a method for passively determining the application of a sample fluid on an analyte strip.

BACKGROUND OF THE INVENTION

The quantification of chemical and biochemical components in colored aqueous fluids, in particular colored biological fluids such as whole blood and urine and biological fluid derivatives such as serum and plasma, is of ever-increasing importance. Important applications exist in medical diagnosis and treatment and in the quantification of exposure to therapeutic drugs, intoxicants, hazardous chemicals and the like. In some instances, the amounts of materials being determined are either so miniscule—in the range of a microgram or less per deciliter—or so difficult to precisely determine that the apparatus employed is complicated and useful only to skilled laboratory personnel. In this case, the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Current teaching counsels diabetic patients to measure their blood glucose level from two to seven times a day depending on the nature and severity of their individual cases. Based on the observed pattern in the measured glucose levels, the patient and physician together make adjustments in diet, exercise and insulin intake to better manage the disease. Clearly, this information should be available to the patient immediately.

Previously, a method widely used in the United States employs a test article of the type described in U.S. Pat. No. 3,298,789 issued Jan. 17, 1967 to Mast. In this method, a sample of fresh, whole blood (typically 20–40 $\mu$l) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

Another previous blood glucose test method employs similar chemistry but in place of the ethylcellulose-coated pad employs a water-resistant film through which the enzymes and indicator are dispersed. This type of system is disclosed in U.S. Pat. No. 3,630,957 issued Dec. 28, 1971 to Rey et al.

In both cases the sample is allowed to remain in contact with the reagent pad for a specified time (typically one minute). Then in the first case the blood sample is washed off with a stream of water while in the second case it is wiped off the film. The reagent pad or film is then blotted dry and evaluated. The evaluation is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator colorimetric determinations in that their result is based on an absolute color reading which is in turn related to the absolute extent of reaction between the sample and the test reagents. The fact that the sample must be washed or wiped off the reagent pad after the timed interval requires that the user be ready at the end of the timed interval and wipe or apply a wash stream at the required time. The fact that the reaction is stopped by removing the sample leads to some uncertainty in the result, especially in the hands of the home user. Overwashing can give low results and underwashing can give high results.

Another problem that often exists in simple lay-operator colorimetric determinations is the necessity for initiating a timing sequence when blood is applied to a reagent pad. A user will typically have conducted a finger stick to obtain a blood sample and will then be required to simultaneously apply the blood from the finger to a reagent pad while initiating a timing circuit with his or her other hand, thereby requiring the use of both hands simultaneously. This is particularly difficult since it is often necessary to insure that the timing circuit is started only when blood is applied to the reagent pad.

In order to eliminate the need for the user to initiate a timing sequence upon application of the blood sample to the reagent pad, U.S. Pat. No. 5,049,487 issued Sep. 17, 1991 to Phillips et al. teaches the use of a reagent pad and reflectance measurement system as illustrated schematically in FIG. 1. The Phillips et al. patent teaches an apparatus for determining the presence of an analyte in a fluid as well as a test strip for use with the apparatus. The fluid to be analyzed is applied to the test strip and the test strip is analyzed by the apparatus. In a preferred embodiment, the test strip comprises a single layer hydrophilic porous matrix 10 to which the chemical reagents are bound. The chemical reagents react with the analyte in the sample applied to the test strip in order to produce a dye that is characteristically absorptive at a wavelength other than the wavelength that the assay medium substantially absorbs. In other works, reaction of the chemical reagent with the analyte produces a color change in the sample.

The reagent matrix 10 is coupled to the underside of an inert test strip carrier 12 containing an orifice 14 therethrough. The analyte sample is applied to the orifice 14 and the apparatus analyzes the opposite side of the test strip by reflecting light from an LED 16 off of the bottom surface of the reagent matrix 10 and sensing the amount of reflected light with a photodiode 18. It is therefore necessary for the sample to diffuse through the test strip prior to being analyzed. In such systems, the amount of time that the analyte is allowed to react with the reagent prior to measurement of a color change is critical to the accuracy of the measurement. The beginning of this "incubation period" must be measured as precisely as possible. In the Phillips et al. patent, as the analyte sample penetrates the reagent matrix 10 and wets the bottom surface, an initial change in reflectance of this measurement surface occurs. The apparatus detects this change in reflectance by sensing a decrease in the amount of light reflected to the photodetector 18. The apparatus then begins the timing of the incubation period upon detection of this change in reflectance. After a predetermined incubation time period, during which the sample containing the analyte reacts with the reagent chemicals in the matrix 10, a second reflectance measurement is made in order to determine the color change in the sample. By accurately measuring the beginning of the incubation period and the time delay before measurement, the accuracy of the apparatus is greatly improved over prior methods.

Because the start of the incubation period in the Phillips et al. method begins with a determination that surface wetting of the underside of the reagent matrix 10 has occurred (in the embodiment of FIG. 1), the processing circuitry coupled to the photodetector 18 must have some method for determining when the reflectance measurements indicate surface wetting. Referring to FIG. 2, there is shown a graph of remission (percent reflection) v. the apparatus system time (in which one unit of system time equals 0.25 seconds of actual time). As can be seen from the graph, the reflectivity of the reagent matrix 10 prior to sample application is a constant value (approximately 88%). After sample application, the reflectivity of the underside of the reagent matrix 10 steadily drops as the sample fluid migrates to the underside of the reagent matrix 10. The remission also drops due to a color change in the reagent caused by reaction with the analyte sample. At some point, the analyte fluid has reached the undersurface of the reagent matrix 10 and further drops in remission are caused only by color change of the reagent. The prior art method analyzes this data in order to make a determination of when surface wetting has occurred on the underside of the reagent matrix 10. This determination is made by sensing when the remission value has dropped by a predetermined, fixed amount from its steady state value prior to sample application. For example, in one commercial version of this prior art system, surface wetting is assumed to have occurred when the remission value drops by approximately 38% (i.e. when a remission value of 50% is observed). When this change in remission (or $\Delta R$) is observed, the prior art device starts the timing of the incubation period, after which the sample measurement will be made.

The prior art method described in Phillips et al. suffers from the problem that the start of the incubation period, by using a fixed reflectance drop, must be tailored to a specific chemistry. A changing in the base reflectance, such as may occur for different enzymes or indicators, requires a predetermination of the fixed reflectance drop. In this sense, a given fixed drop is not generally applicable to different systems.

There is therefore a need for a system and method for determining the application of a sample fluid on an analyte strip which is effective for use with any analyte strip, regardless of the specific chemistry or strip-to-strip variations therein. The present invention is directed toward meeting this need.

SUMMARY OF THE INVENTION

The present invention relates to a method for passively determining the application of a sample fluid on an analyte strip using measurement of ambient light passing through the strip. Sample fluid, such as whole blood, is applied to a reagent matrix and the amount of ambient light transmitted through the matrix is periodically measured both before and after application of the sample fluid. A step increase of the transmitted light reading occurs after hydration of the strip, and the occurrence of this step increase is used to start a predetermined incubation period. At the expiration of the incubation period, another light transmission measurement is made which is indicative of an analyte concentration in the sample fluid (such as glucose concentration in a whole blood sample).

In one form of the present invention, a method for determining a start of reaction timing for measurement of a reaction between a sample fluid and a reagent is disclosed, comprising the steps of a) measuring a transmission of light through the reagent at intervals prior to application of the sample fluid to the reagent; b) applying the sample fluid to the reagent; c) measuring the transmission of light through the reagent/sample fluid combination at intervals after performing step (b); d) determining a location of a step increase in the measurement data taken at steps (a) and (c); e) beginning a predetermined time period at a time corresponding to the step increase; and f) measuring the transmission of light through the reagent (sample fluid combination after expiration of the predetermined time period.

DETAILED DESCRIPTION OF THE PREFERRED EMBODIMENTS

Figure 1:
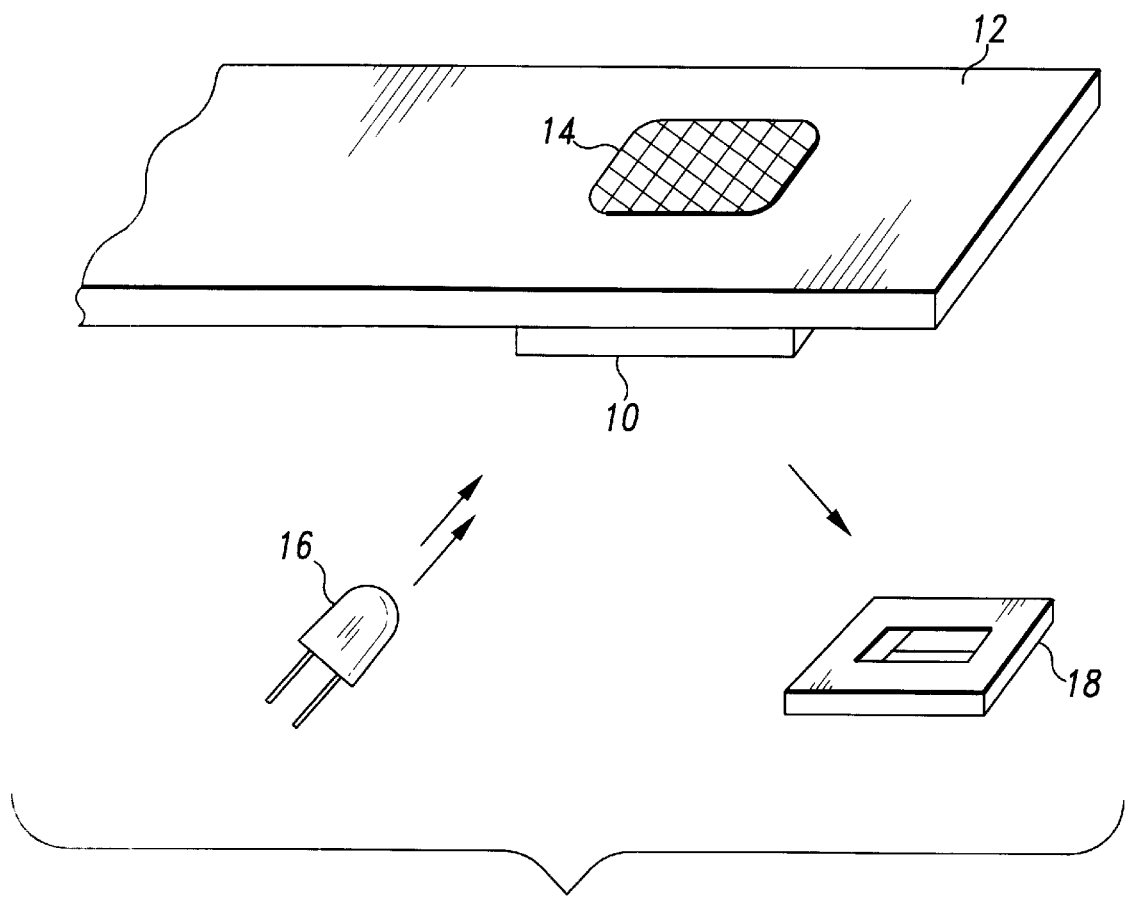
FIG. 1 is a schematic perspective view of a prior art optical reflectance analyte measurement system.

For the purposes of promoting an understanding of the principles of the invention, reference will now be made to the embodiment illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Figure 2:
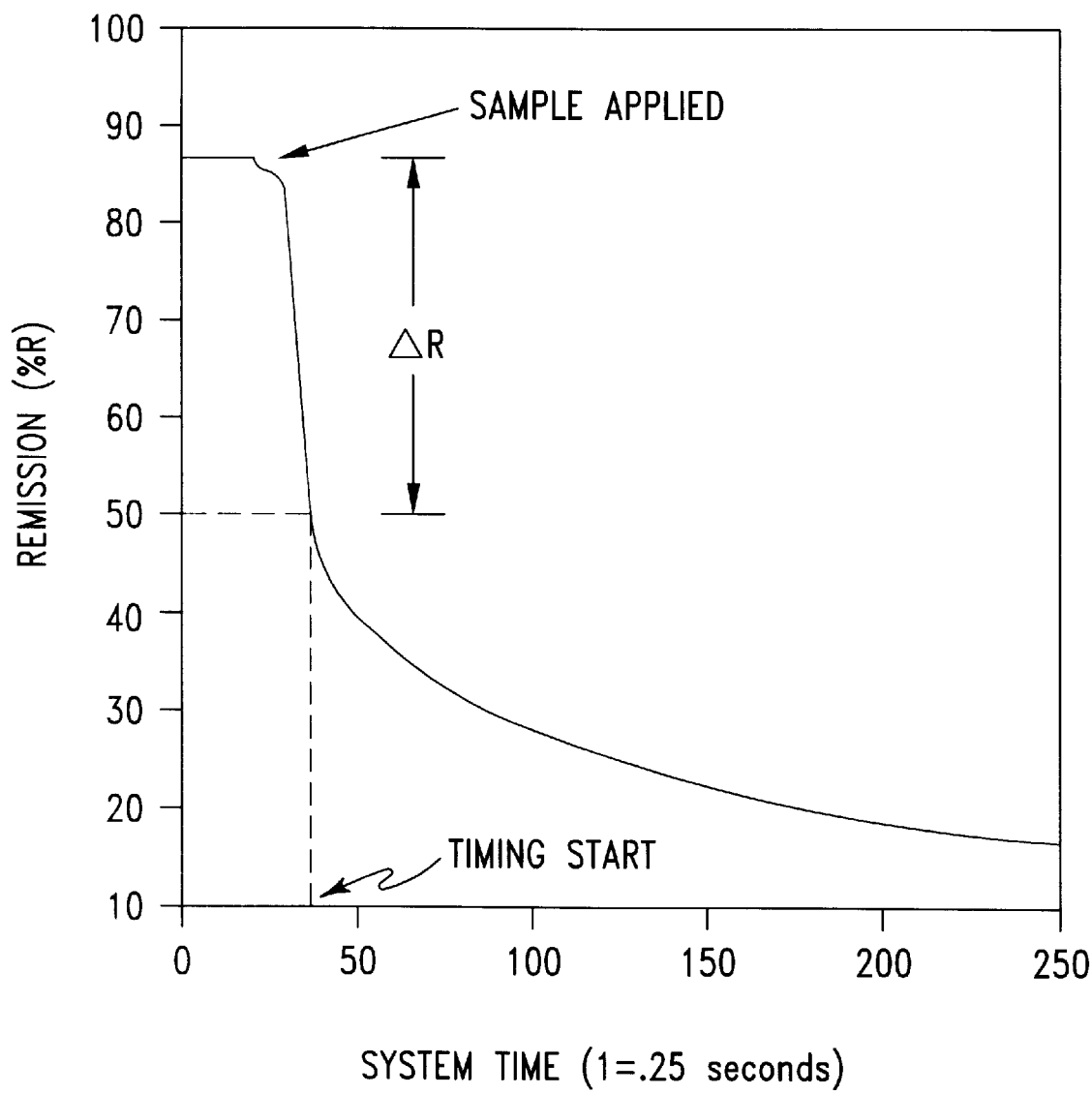
FIG. 2 is a graph of remission v. system time, illustrating a prior art method for determining a start of the reaction incubation period in an optical reflectance meter.
Figure 3:
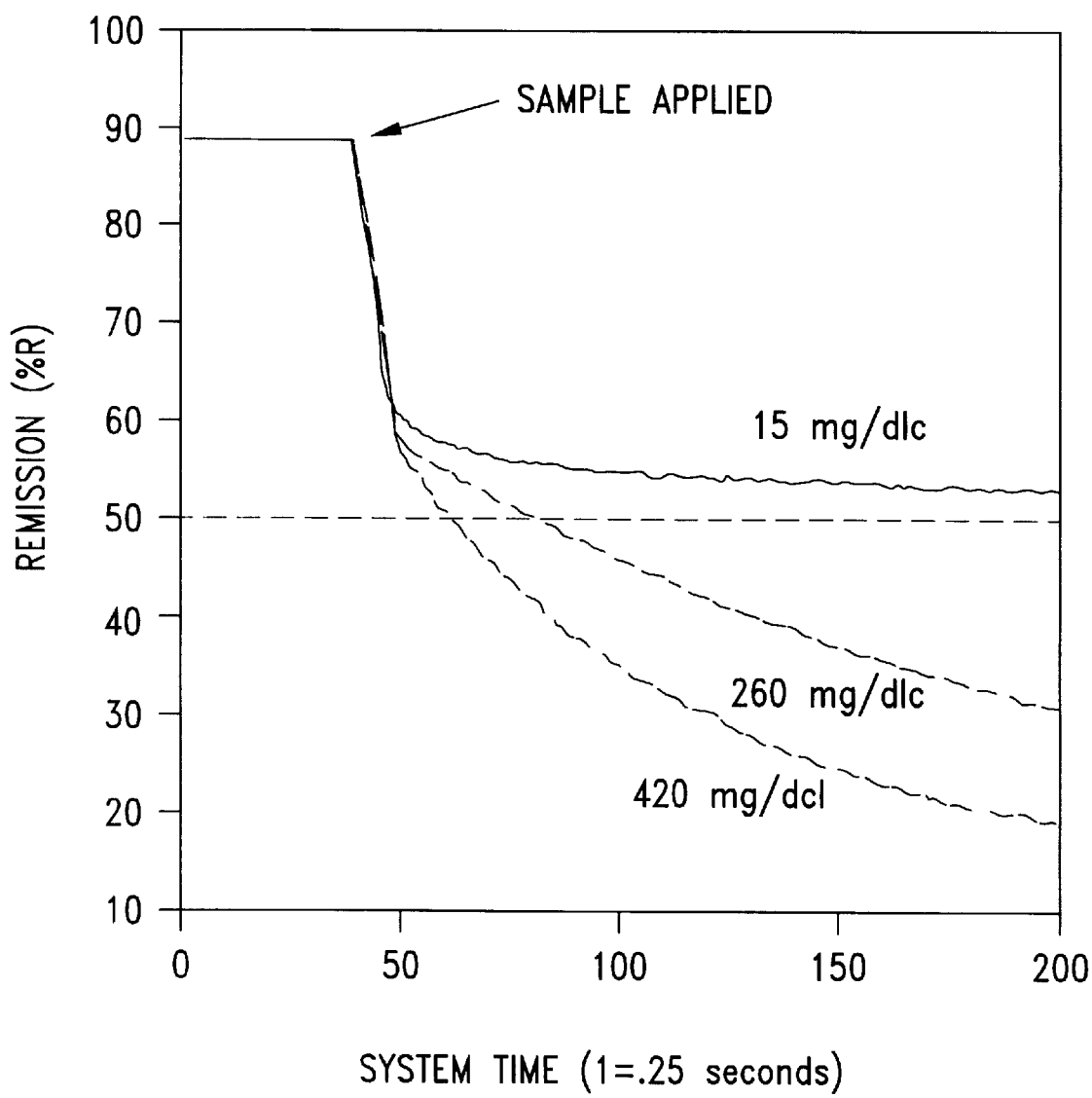
FIG. 3 is a graph of remission v. system time for several different analyte samples.

FIG. 3 illustrates the problem with establishing the start of the incubation period with a predetermined drop in remission. It is characteristic of remission v. time data for a whole blood sample to exhibit the general shape of the curve of FIG. 3. However, FIG. 3 plots the remission v. time data for several different whole blood samples, illustrating that the minimum remission value and the speed with which the graph transitions to the minimum remission value is highly variable and dependent upon several factors, including the glucose concentration within the sample. Therefore, while picking a predetermined drop in remission value in order to start the incubation period may work well when the remission v. time graph has the expected form (as in FIG. 2), this method may not work well when the remission v. time graph for different glucose samples varies widely, as shown in FIG. 3. The 50% remission threshold of FIG. 2 is not effective for the varying curves of FIG. 3, as plainly evident from an examination of this figure. In fact, one of the remission v.

time curves never reaches the 50% remission value. Utilizing a predetermined drop in remission as the start of the incubation period is therefore undesirable in many real-world test scenarios. For the chemistry of FIG. 3 it is obvious that reducing the magnitude of the predetermined drop will cause a start time to be triggered for all three curves. However, it is by no means certain that the same magnitude will be valid for a chemistry where the background material has a different density, or the enzyme-indicator mix has a different base color. In theory, it is possible that n different strip lots could require n different "predetermined" drops.

Figure 4:
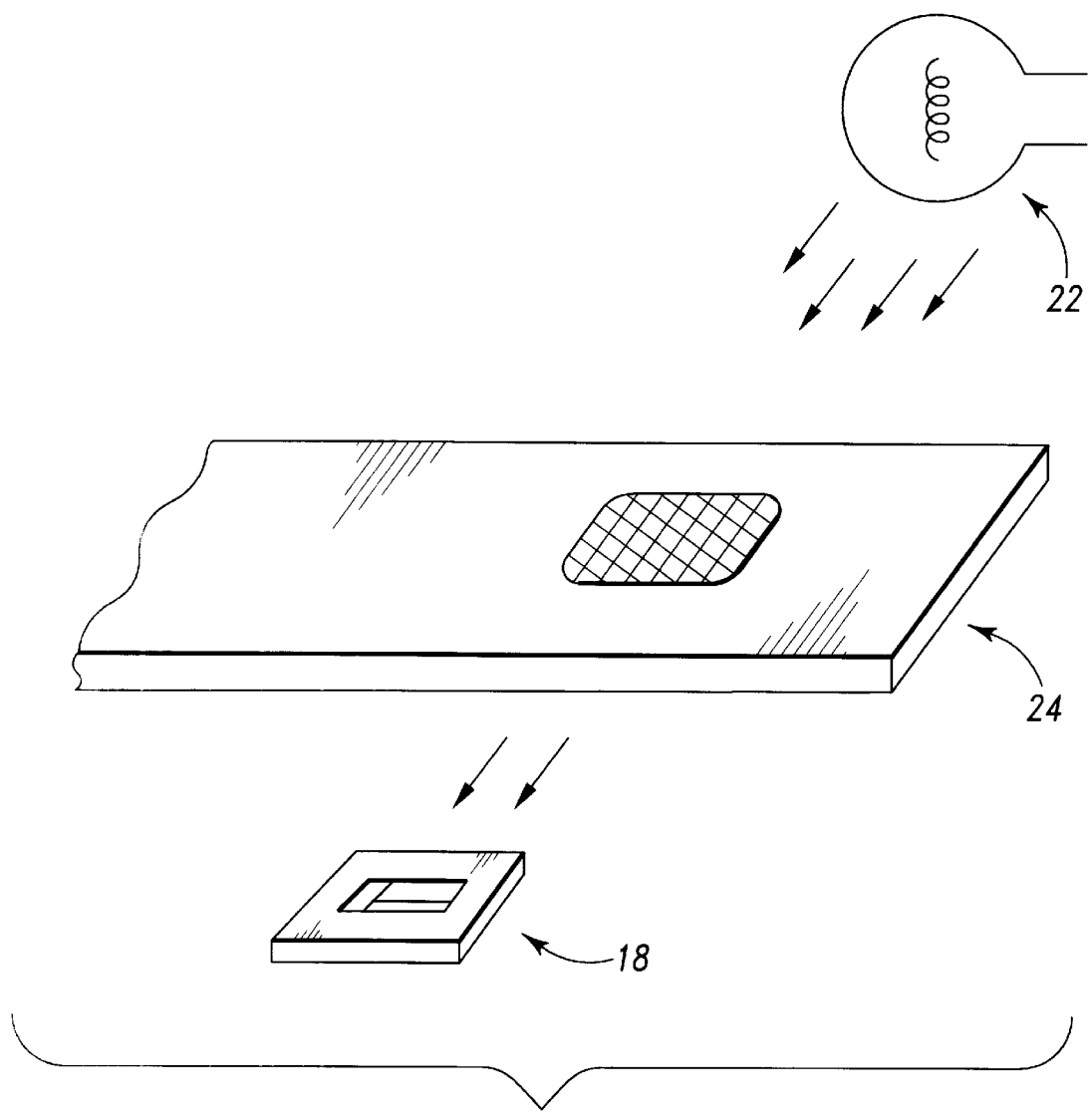
FIG. 4 is a schematic perspective view of a preferred embodiment apparatus of the present invention for passively determining the application of a sample fluid on an analyte strip.

The present invention relies upon physical changes that occur to the reagent strip upon wetting of the bottom surface to signal the start of the incubation period. FIG. 4 illustrates a preferred embodiment apparatus of the present invention for passively determining the application of a sample fluid on an analyte strip, the apparatus being indicated generally at 20. As can be seen from the figure, the apparatus 20 requires only a detector 18, and not a dedicated illumination source 16, as in the prior art system of FIG. 1.

Instead, the system 20 utilizes the ambient light 22 present in the room where the system 20 is located as the light source for the detector 18. The system 20 utilizes a reagent strip 24 in which the sample fluid is applied to the top surface 26 and soaks through to the bottom surface 28. The sample fluid contains an analyte that reacts with the reagent contained within the strip 24 to produce a color change. This color change may then be measured by any desired means, such as by the detector 18.

Because the system 20 uses only ambient light 22 and contains no internal light source, it is to be expected that the intensity level of such ambient light 22 will vary from measurement to measurement, depending upon the ambient conditions surrounding the system 20 at the time of each use. In order to compensate for such varying lighting conditions, the output of the photodetector 18 may be periodically sampled and integrated by a microprocessor (not shown). The integration time of the photodetector 18 output signal may be adjusted in order to compensate for the ambient light 22 level, using a longer integration time for low ambient light 22 levels and a shorter integration time for high ambient light 22 levels. In this manner, the system 20 will work in a variety of ambient light 22 levels.

In order to determine the start of the incubation period, the system 20 relies upon the realization that upon hydration (the soaking through of the sample fluid to the bottom surface 28), the transmission coefficient (probability of forward scattering of the ambient light 22) of the reagent strip 24 increases substantially. This increase in light transmission is seen as a step increase in the light observed by the photodetector 18 through the reagent strip 24.

Figure 5:
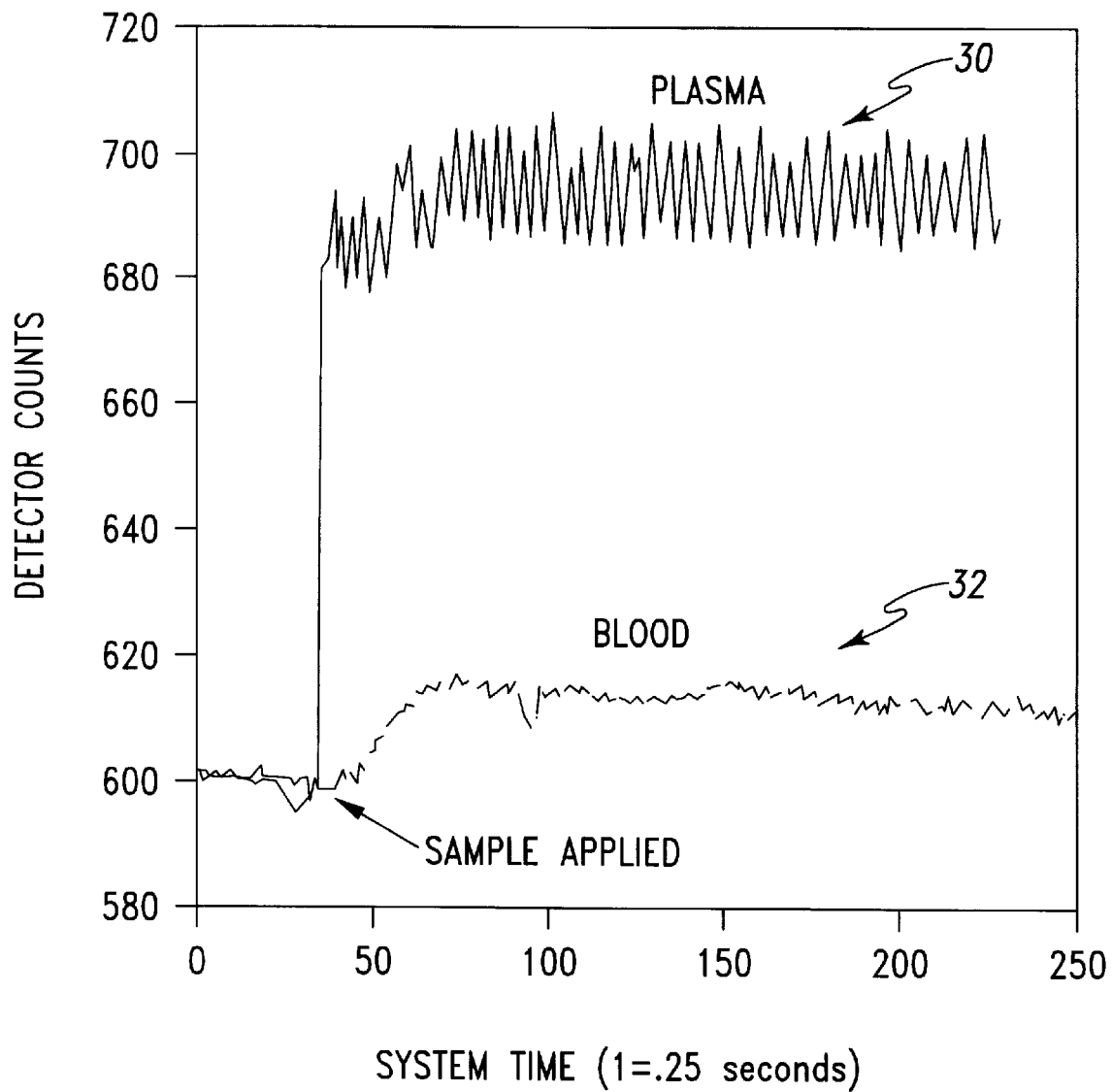
FIG. 5 is a graph of detector counts v. system time, illustrating a preferred embodiment method of the present invention for determining a start of the reaction incubation period.

FIG. 5 illustrates the response of the photodetector 18 when blood plasma is applied to the reagent strip 24 (upper curve 30), and when whole blood is applied to the reagent strip 24 (lower curve 32). The large difference in the magnitudes of the blood response curve 32 and the plasma response curve 30 is due to the difference in the opacity of the two fluids (i.e. the plasma exhibits a much smaller absorption coefficient). This difference can be used by the system 20 to determine whether blood or a plasma-like control solution has been applied to the reagent strip 24.

As can be seen from the curves 30 and 32, application of the sample to the reagent strip 24 causes hydration of the reagent strip 24 membrane, thereby increasing its transmission of ambient light 22 to the photodetector 18. This is seen as a step increase in the output of the photodetector 18. This step increase may be detected by the microprocessor of the system 20 and used to begin timing of the incubation period. A step increase may be defined as an increase in the measurement data by more than a predetermined amount or by more than a predetermined percentage. It will be noted with reference to FIG. 5 that the magnitude of the step increase in the plasma curve 30 is much more dramatic than the step increase in the blood curve 32.

Figure 6:
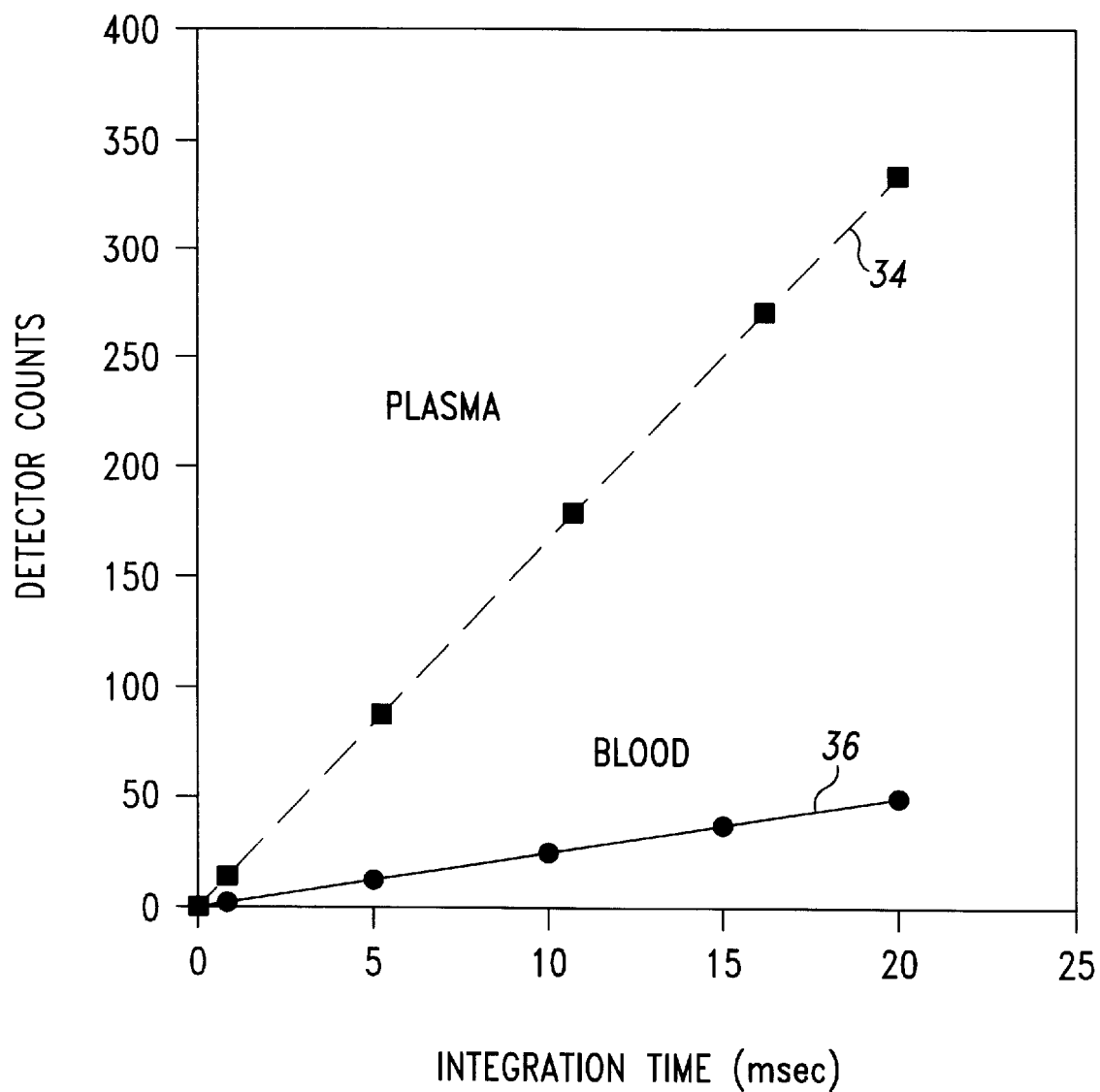
FIG. 6 is a graph of detector counts v. integration time, illustrating a method of increasing the signal-to-noise ratio of the present invention.

As described hereinabove, the system 20 may compensate for differing amounts of ambient light 22 at the time of the measurement by changing the integration time of the output from the photodetector 18. FIG. 6 shows the photodetector 18 response as a function of integration time for both plasma (upper curve 34) and blood (lower curve 36) hydration of a membrane-type colormetric strip 24. The plotted value is the difference between the unhydrated response (dry strip 24) and the maximum hydrated response. As is evident from the data of FIG. 6, by increasing the integration time, it is possible to increase the signal-to-noise ratio of the measured response, thereby improving the detectivity in low ambient light conditions, making the system 20 more robust to its operating environment at the time of measurement.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for determining a start of reaction timing for measurement of a reaction between a sample fluid and a reagent, comprising the steps of:

a) measuring a transmission of light through the reagent at intervals prior to application of the sample fluid to the reagent;

b) applying the sample fluid to the reagent;

c) measuring the transmission of light through the reagent/sample fluid combination at intervals after performing step (b);

d) determining a location of a step increase in the measurement data taken at steps (a) and (c);

e) beginning a predetermined time period at a time corresponding to the step increase; and f) measuring the transmission of light through the reagent sample fluid combination after expiration of the predetermined time period.

2. The method of claim 1, wherein the sample fluid is whole blood.

3. The method of claim 2, wherein the reagent reacts with the whole blood to produce a color change in proportion to an amount of glucose in the whole blood.

4. The method of claim 1, wherein step (a) comprises measuring an amount of ambient light transmitted through the reagent.

5. The method of claim 1, wherein steps (c) and (f) comprise measuring an amount of ambient light transmitted through the reagent.

6. The method of claim 1, wherein the intervals are fixed intervals.

7. The method of claim 1, further comprising the steps of:

g) determining a magnitude of the light transmission measured at step (a); and h) adjusting an integration time of subsequent measurements based upon the magnitude determined at step (g).

* * * * *